455-602    AU 263    EX
11/26/85    XR    4,555,631

United States Patent [19]
Martens

[11] Patent Number: 4,555,631
[45] Date of Patent: Nov. 26, 1985

[54] APPARATUS FOR TRANSMITTING SIGNALS BETWEEN TWO RELATIVELY ROTATABLE PARTS

[75] Inventor: Gerhard Martens, Hamburg, Fed. Rep. of Germany

[73] Assignee: U.S. Philips Corporation, New York, N.Y.

[21] Appl. No.: 464,544

[22] Filed: Feb. 7, 1983

[30] Foreign Application Priority Data
Feb. 12, 1982 [DE] Fed. Rep. of Germany ....... 3205065

[51] Int. Cl.⁴ .............................................. G02B 27/00
[52] U.S. Cl. ..................................... 250/551; 455/602
[58] Field of Search ................. 250/231 SE, 231 GY, 250/237 G, 551; 340/347 P; 356/395; 455/602; 350/96.15

[56] References Cited
U.S. PATENT DOCUMENTS
3,612,695  10/1971  Bouwhuis ....................... 250/237 G OTHER PUBLICATIONS
Heil and Wolf, An Electrooptical Rotating Data Transmitter, Jul. 1979, pp. 233/237.

Primary Examiner—David C. Nelms
Assistant Examiner—James Gatto
Attorney, Agent, or Firm—Jack E. Haken

[57] ABSTRACT

An optical transmission system arrangement for transmitting data between two relatively rotatable parts. A hollow cylinder with a mirror-coated inner surface onto which the light is incident at the smallest possible grazing angle and is frequently reflected. The light is coupled in and out through a coupling section in the hollow cylinder, at which the light is incident onto the inner surface. The system achieves a comparatively low damping because the reflecting power at small angles of incidence is comparatively high.

9 Claims, 7 Drawing Figures

APPARATUS FOR TRANSMITTING SIGNALS BETWEEN TWO RELATIVELY ROTATABLE PARTS

The invention relates to apparatus for transmitting signals between two relatively rotatable parts comprising a light-emitting device and a lightreceiving device, which are each fixedly arranged with respect to one of the two parts, and a mirror arranged concentrically to the axis of rotation for reflecting at least one beam of radiation around the axis of rotation.

Such an apparatus is essentially known from the German Patent Specification No. 21 13 690. In this case, the mirror has a toroidal form and is subdivided into two halves, one half being connected to the rotor and the other half to the stator. The light-receiving device is arranged on the stator and receives two beams of radiation which are emitted by two light-emitting diodes and circulate in opposite senses through the mirror around the axis of rotation, these beams being constantly reflected to and fro between the fixed part and the rotating part of the mirror.

The two beams of radiation are then reflected at comparatively large grazing angles (the grazing angle is the angle which is enclosed by a light ray with the line tangent to the mirror surface). Since with a real mirror, the reflecting power decreases with increasing grazing angle, the beams of radiation are comparatively strongly damped. In the known arrangement, the beams of radiation have a comparatively large angle of aperture. The path covered by one of the outer limiting rays of the beam of radiation from the lightemitting device to the light-receiving device greatly differs from the path of the central ray of the beam of radiation so that a pulse emitted by the light-emitting device appears in a considerably wider form at the output of the light-receiving device. A further disadvantage of the known arrangement finally consists in that, when the light-emitting device is arranged immediately in front of the light-receiving device, the light cannot reach the light receiver directly, but only after a nearly complete cycle. If, however, the rotor is rotated further through a given angle, the radiation of one of the light-emitting diodes can reach the light receiver directly. Delay jumps then occur, which render a continuous signal transmission at a high transmission speed much more difficult.

The invention has for its object to provide an arrangement of the kind mentioned in the opening paragraph, in which beams of radiation are damped only to a comparatively small extent and the pulse widening is limited.

The apparatus according to the invention is therefore characterized in that the mirror is constructed as a hollow cylinder provided on the inner side with reflecting surfaces and enclosing a part which rotates relative to the mirror and on which the light-emitting or light-receiving device is arranged, in that the beam of radiation is incident at the smallest possible grazing angle onto the inner surface of the hollow cylinder, and in that the hollow cylinder has a coupling section through which the light-receiving or light-emitting device fixedly arranged with respect to the hollow cylinder is in optical connection with the light-emitting device and the light-receiving device, respectively, on the rotating part and whose arc length is proportioned so that in each position of the rotating part relative to the hollow cylinder at least part of the beam of radiation reaches the coupling section.

The term "hollow cylinder" is to be understood here and in the following description to mean a hollow body the inner surface of which is formed so that with surfaces at right angles to the axis of rotation only circles are obtained as sectional figures. The beams of radiation are, in contrast with the known arrangement, invariably reflected only at a surface, i.e. at the inner surface of the hollow cylinder. The damping is comparatively low because the separate rays of the beam(s) of radiation are incident at a small grazing angle (in a plane at right angles to the axis of rotation) and because the reflecting power increases with decreasing grazing angle. The difference in delay between the marginal rays of a beam of radiation is then very small so that the electrical pulses derived from the emitted light pulses in the light receiver have hardly widened. The transmission capacity may still be increased in that transmissions take place in several data channels with differently coloured light. When the term "light" is used in connection with the invention, this term is to be understood to mean here and in the following description not only visible light but also especially infrared or ultraviolet light.

When only a separate beam of radiation is used for the data transmission from the light-emitting device to the light-receiving device, it is possible that, as in the known arrangement, delay jumps occur, which correspond to the delay of the beam of radiation through nearly the whole circumference of the hollow cylinder. According to a preferred embodiment of the arrangement in accordance with the invention, these delay jumps can be avoided in that two beams of radiation having opposite directions of circulation around the axis of rotation are reflected and in that invariably at least one beam of radiation or a part of a beam of radiation reaches the coupling section. When the light receiving device or the light-emitting device on the rotating part moves towards the coupling section, the delay of the light gradually decreases towards the receiver until the light emitter or light receiver is positioned directly in front of the coupling section, after which this delay increases again. Consequently, the delay varies continuously and there are no delay jumps.

Essentially, two light-emitting or light-receiving elements can be arranged at the area of the coupling section. The two elements can be connected parallel to one another; however, the element may also be always switched into circuit which is associated with the beam of radiation with the shorter delay time. A further embodiment of the arrangement in accordance with the invention, however, needs only one such element at the area of the coupling section due to the fact that at the area of the coupling section two radiation deflection systems are arranged which conduct the two beams of radiation moving in opposite directions from or to a single light-emitting or light-receiving element located outside the hollow cylinder into the hollow cylinder or out of it.

When the unit arranged on the part rotatable relative to the hollow cylinder (which unit is a light-emitting device or a light-receiving device) is located accurately in front of the coupling section or in a position displaced through 180° with respect to this coupling section, the delay times of the two beams of radiation are equally long. In any other position, however, different delay times are obtained so that upon the occurrence of a light pulse in the light-receiving device two signals electrically relatively displaced in time are produced, the last arriving signal generally having a lower amplitude, due to the fact that it is reflected more frequently. A further decrease of the amplitude of the said signal can be obtained according to a further embodiment of the invention in that there is provided in the hollow cylinder opposite to the coupling section a non-reflecting section which is smaller than the coupling section. When the non-reflecting sector is made accurately so large that half of each of the two beams of radiation impinges on this sector when the two beams of radiation extend symmetrically thereto, the second signal is damped additionally by at least 3 dB.

A further embodiment of the arrangement according to the invention is characterized in that the two beams of radiation are displaced with respect to each other in the direction parallel to the axis of rotation. This embodiment permits of processing the two beams of radiation separately.

In a further elaboration of this embodiment, it is ensured that in the path of the beam in front of the light-receiving device are arranged two crossing mirrors or prisms which are displaced relatively in the direction parallel to the axis of rotation and which join the beams of radiation arriving from two sides and supply them, as the case may be, through a light conductor device to the light-receiving device. Especially when the light-emitting device is arranged on the part rotatable relative to the hollow cylinder, at the area of the open ends of these two curved mirrors the beams of radiation can be further processed by means of comparatively simply constructed optical elements.

The invention will now be described more fully with reference to the drawing.

Figure 5A:
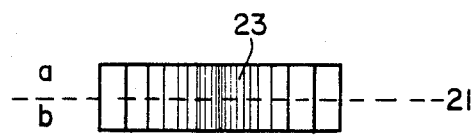

FIG. 5a, b, c show in side elevation an element for damping the primary intensity at the area of the coupling section.

Figure 1:
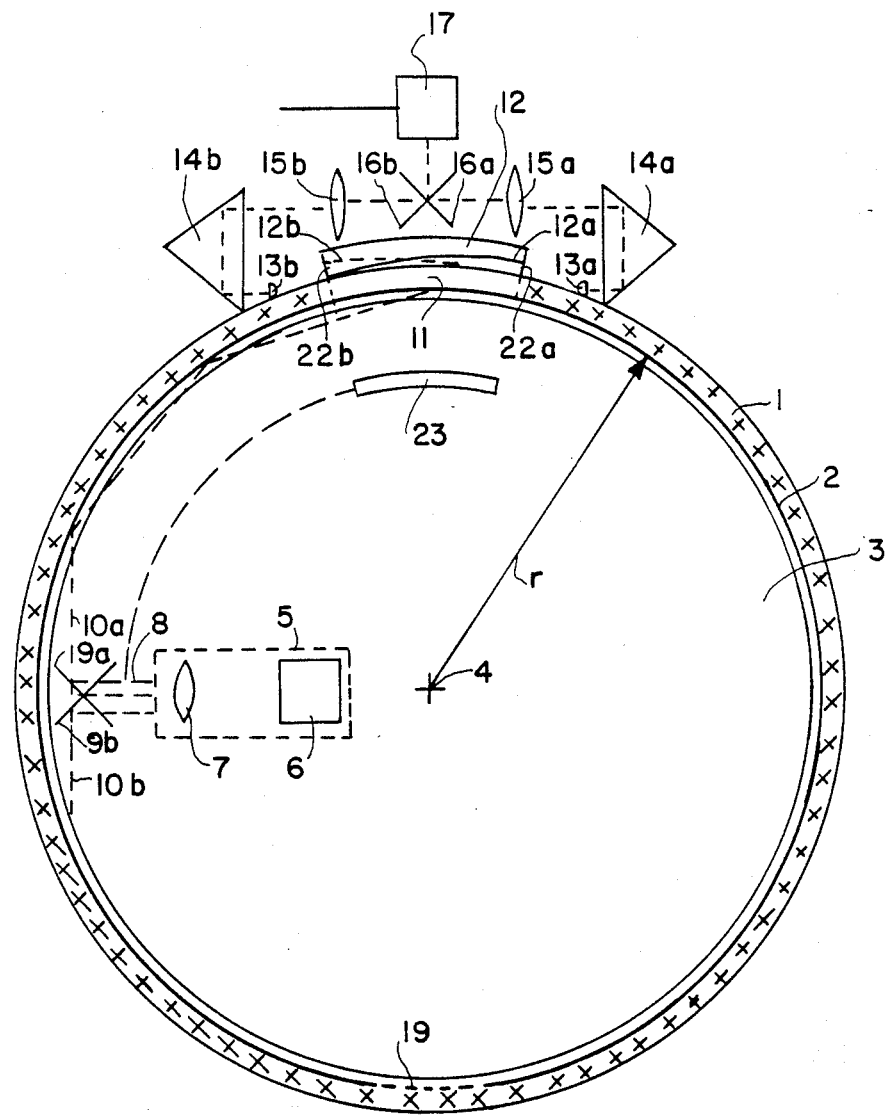
FIG. 1 shows an embodiment of the arrangement according to the invention.

FIG. 1 shows a hollow cylinder of circular cross-section, the cylindrical axis 4 of which is at right angles to the plane of the drawing. The hollow cylinder 1 may be made, for example, of glass. On its inner side, this cylinder is provided with a reflecting layer 2 substantially along the whole circumference. The hollow cylinder is not rotatable.

The hollow cylinder encloses a rotatable part 3, for example, in the form of a disc, which is arranged parallel to the plane of the drawing and whose axis of rotation 4 is identical to the cylindrical axis of the hollow cylinder 1. On the disc 3 is arranged a lightemitting device 5, which comprises a light-emitting element 6, for example, a laser or a light-emitting diode, as well as a suitable optical system 7, which produces from the emitted light a beam 8 of rays extending parallel to the plane of the drawing, this beam having a finite cross-section (for example, 5 mm in the direction at right angles to the plane of the drawing and 5 mm in the direction parallel thereto). The beam of radiation 8 reaches two crosswise arranged flat mirrors 9a and 9b which are at right angles to the plane of the drawing and which are likewise connected to the disc 3, but which are relatively displaced in the direction of the axis 4 so that the beam of radiation 8 is split into two oppositely extending beams of radiation 10a and 10b, which extend parallel to the plane of the drawing. Alternatively, prisms may be used instead of the mirrors.

The two beams of radiation 10a and 10b are reflected several times at the reflecting inner surface 2 of the hollow cylinder 1 and consequently they fan out in radial direction to an optical pattern or an optical channel. As the value of the maximum grazing angle $\beta$ of the reflections and the value of the radius r of the hollow cylinder are larger, the width (dimension in radial direction) D of the optical pattern or the optical channel is larger. Use is made of the formula $$\beta = \sqrt{2D/r} \tag{1}$$

The mirrors 9a and 9b have to be aligned in such a manner and have to be mounted so close in front of the reflecting layer 2 that the beams of radiation 10a and 10b are incident at the smallest possible grazing angle onto the reflecting inner surface of the hollow cylinder. The value $\beta$ and hence also the radial width of the optical channel are then as small as possible. The reflecting power is independent of the radius of the hollow cylinder if the condition $\sin \beta = \beta$ is satisfied at least on approximation. If $\beta$ is considerably larger, the reflection losses increase considerably with the radius of the hollow cylinder. The maximum grazing angle $\beta$ would therefore not be allowed to exceed 12°. The width D of the optical channel is of the order of 1 mm.

The beam of radiation 10a reaches after several reflections an arc 11—which in the following description will be designated as coupling section—in which the reflecting layer 2 is interrupted. The arc length g of this coupling section corresponds to the formula $$g = 2 \cdot \sqrt{2Dr} \tag{2}$$

Figure 2:
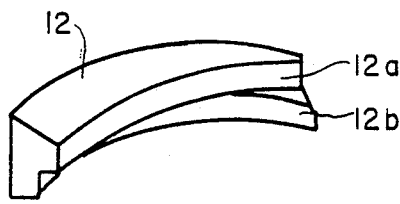
FIG. 2 is a perspective view of the curved mirrors.

The channel width D in this equation can be eliminated by means of the aforementioned formula for $\beta$ so that the following equation is obtained:

$$g = 2r\beta \tag{3}$$

or in other words: the angle at the centre of the coupling section is twice as large as the maximum grazing angle. When the arc length is chosen to be smaller, a part of the light of the beams of radiation 10a and 10b is reflected through the coupling section to the reflecting surface 2 so that this part cannot be evaluated. When g is chosen to be considerably larger, it becomes considerably more difficult to determine the light rays diaphragmed out. The beam of radiation incident onto the coupling section 11 is refracted on the glass inner surface and emanates again the inner side of the hollow cylinder 1 so as to be displaced approximately in parallel direction. The beam them reaches a coupling-out mirror 12 which is shown in detail in FIG. 2. The mirror 12 has a curved reflecting surface 12a which is arranged above a curved reflecting surface 12b (which consequently is shown in elevation in FIG. 1 in front of the surface 12b indicated by a broken line) and which intersects the surface 12b approximately at the centre. The radius of curvature of the two surfaces is approximately 4/3 r, r being the radius of the hollow cylinder. The coupling-out mirror 12 is aligned with respect to the reflecting layer 2 so that the line tangent to the lefthand end of the surface 12a coincides with the line tangent to the reflecting layer 2. This also applies to the righthand end of the reflecting surface 12b. For the sake of clarity of the drawing, the latter is not to scale and the surfaces 12a and 12b are not drawn in line with the reflecting layer 2.

It is achieved by this arrangement that the beam of radiation passing through the glass sector in the coupling section can be conducted outwards completely and as far as the emanation aperture 22a and 22b, respectively, without an additional increase of the channel width D and of the radiation divergence, that is to say that the light beam 10a is conducted outwards through the mirror 12a, whilst the light beam 10b is conducted outwards through the mirror 12b. It is then assumed that the mirrors 9 and 12a are separated by the same plane of the mirrors 9b and 12b extending parallel to the plane of the drawing in FIG. 1. This plane also separates the beams of radiation 10a and 10b.

With the choice of the radius of curvature of 4/3 r, the width of the emanation apertures 22a and 22b, through which the rays emanate from the hollow cylinder, is accurately equal to the width D of the optical channel. The beams of radiation can therefore leave the emanation apertures without hindrance. When the radius of curvature of the mirror surfaces 12a and 12b is smaller than 4/3 r, a part of the light arriving at the coupling section is reflected back into the hollow cylinder. When the radius of curvature of the two reflecting surfaces is made larger than 4/3 r, the emanating beams are widened proportionally to the radius of curvature of the coupling-out mirrors, which renders the subsequent collimation of the beams of radiation more difficult.

An advantage of the embodiment shown is that through the coupling section no contaminations can reach the cylinder mirror. A further advantage is that the coupling-out mirror 12 is adjustable in a very simple manner in radial direction because it has to be pressed only against the outer wall of the hollow cylinder. However, the reflections and multiple reflections occurring in the glass arc of the coupling section and leading to a damping of the light intensity and to a widening of the light pulses are disadvantageous.

This disadvantage can be avoided if the wall portion of the hollow cylinder at the area of the coupling section is left out and the coupling-out mirror is displaced in radial direction to the interior so that on the lefthand end of the mirror surface 12a and on the righthand end of the mirror surface 12b the line tangent to the mirror surface coincides with the lines tangent to the mirror surfaces coincides with the lines tangent to the inner surface of the hollow cylinder.

The radiation coupled out by means of the mirror surfaces 12a and 12b is conducted through a cylindrical lens 13a and 13b, respectively, with a short focal distance, which collimates the light diverging in the plane of the drawing on a prism 14a and 14b, respectively. By means of a collector lens 15a and 15b, respectively, and through a mirror or prism 16a or 16b, respectively, there is produced on the entrance surface an image of a light-receiving device 17 common to both radiation paths, which comprises an optical system (not shown further) similar to that of the light-emitting device 5, which focuses the light pulses onto a suitable converter which converts the light into an electrical signal, or onto a light-conducting fibre or fibre bundle which is coupled to a converter.

Figure 4:
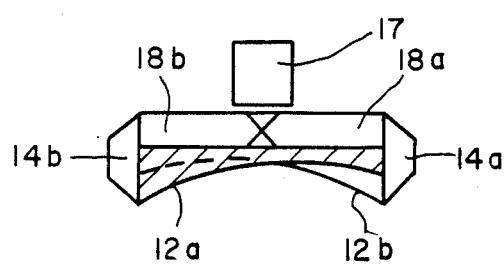
FIG. 4 is a plan view of a preferred embodiment of the unit arranged behind the coupling section.

Instead of the prisms 14a and 14b, use many alternatively be made of two flat mirrors. Advantageously, the light can also be conducted from the base surface of the prisms 14a and 14b, respectively, to the input of the light-receiving device 17 through two prismatic rods 18a and 18b, as is shown in FIG. 4, which are bevelled at the area of the input of the light-receiving device and are butt-jointed to the base surface of the prisms 14a and 14b. In this case, not only the lenses 15a and 15b and the mirrors 16a and 16b, but also the cylindrical lenses 13a and 13b can be omitted.

The separate light rays of a beam of radiation 10a and 10b, respectively, cover different path lengths during a half cycle on the mirror surface of the hollow cylinder, but the differences are very small; they can be at most equal to the width D of an optical channel and a beam of radiation, respectively. The delay differences resulting therefrom are therefore generally negligible (and are moreover independent of the ray). However, the beams of radiation 10a and 10b each cover different distances in dependence upon the position of the light-emitting device with respect to the hollow cylinder 1; in the extreme case, this difference corresponds to the inner circumference of the hollow cylinder 1, from which result comparatively large delay differences. With high pulse frequencies (>800 MHz and with r=0.5 m), the possibility could then arise that a light pulse in the shorter path has already reached the coupling section before the preceding light pulse has arrived there through the longer path. This could render the evaluation much more difficult.

In order to facilitate the evaluation, a non-reflecting sector 19 indicated by broken lines is arranged on the hollow mirror opposite to the coupling section 11. A part of the radiation beam, which has to cover the longer path—in the position of the light-emitting device shown in FIG. 1 this is the radiation beam 10b—, is absorbed by this non-reflecting sector 19. When the arc length of the non-reflecting sector 19 is chosen so that it corresponds to the coupling-out length L of a luminous signal having the width D/2 ($L=2\sqrt{Dr}=g/\sqrt{2}$), the radiation beam, which reaches the coupling section via this sector, is damped by at least 3 dB. The amplitude difference thus obtained of the luminous pulses arriving through the two different paths at the light-receiving device 17 can be used by means of a suitable electronic evaluation system for suppressing the pulse having the longer delay.

Figure 3:
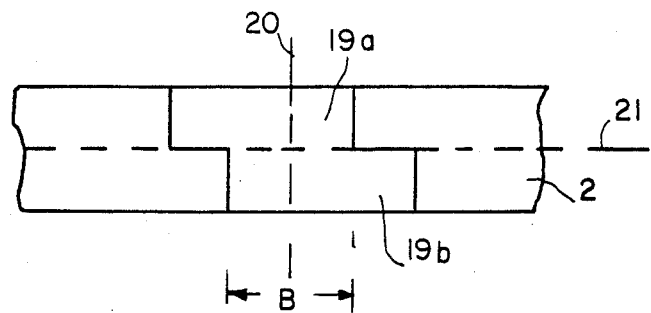
FIG. 3 is a side elevation (viewed from the axis of rotation) of a part of the hollow cylinder.

In the embodiment of FIG. 3, which is an elevation of the hollow cylinder 1 from the axis 4, the radiation beam having the longer delay can even be completely suppressed. The central line 20 is located accurately opposite to the centre of the coupling section. The line 21 and the plane containing this line, respectively, divides the hollow cylinder 1 into two halves, all the elements provided with the subscript a being associated with the upper half and all the elements provided with the subscript b being associated with the other half. The line 21 moreover separates two overlapping non-reflecting parts 19a and 19b on the inner surface of the hollow cylinder (the overlapping region is designated by B and its centre coincides with the line 20). When the length of each of these parts is at least equal to the coupling-out length g and when the overlapping region B at least approximately corresponds to the value $g/\sqrt{2}$, this results in the following operation:

If, as shown in FIG. 1, the light-emitting device occupies a position in which the central axis of the radiation beam 8 arrives on the righthand side of the line 20, the radiation beam 10a arrives at the coupling section 11 solely through reflecting surfaces, whilst the radiation beam 10b is absorbed completely by the non-reflecting part 19b. If the light-emitting device 5 occupies a position in which the central axis of the radiation beam 8 intersects the line 20, the parts 19a and 19b each time absorb half the radiation beams 10a and 10b, respectively. The other halves circulate through the righthand upper part and through the lefthand lower part, respectively, and reach the coupling section after having traversed each time the same path length. If the light-emitting device is still further rotated counterclockwise (the central axis of the radiation beam passes through the hollow cylinder and then further on the lefthand side of the axis 20), a gradually increasing part of the radiation beam 10a is absorbed by the part 19a, whereas the part of the radiation beam 10b absorbed by the part 19b gradually decreases until in the end the radiation beam 10a has been absorbed completely and the radiation beam 10b is no longer influenced by the part 19b. The part 19 consequently causes a change of tracks, that is to say the transition of the data transmission from the radiation beam 10a to the radiation beam 10b, or conversely, in dependence upon the sense of rotation.

Thus, the electronic evaluation system can be considerably simplified. On the other hand, more sophisticated means are required for the adjustment of the light-emitting device in such a manner that the radiation beam 10a constantly extends above the line 21 and the radiation beam 10b constantly extends below this line.

The light intensity which reaches the coupling section and hence impinges on the light-receiving element 17 corresponds in nearly all the positions of the rotor to half the light intensity of the light-emitting device and to the whole light intensity of only one radiation beam 10a and 10b, respectively, if reflection losses on the hollow mirror 2 are left out of consideration. However, if the rotor is arranged on the righthand side in front of the coupling section, both radiation beams reach the receiving element 17 through the coupling-out mirror and the optical systems arranged behind it and charge it with a double intensity. These intensity jumps may give rise to difficulties especially at high data speeds in the electronic evaluation system, which difficulties can be avoided only by the use of a large plurality of electronic means. However, these difficulties can be avoided in that in front of the coupling section is arranged an element 23 which is rigidly connected to the hollow cylinder and whose cross-section represents an arc of a circular ring. The radial distance of this element from the coupling section is proportioned so that upon rotation of the rotor the crossing mirrors 9a and 9b are conducted between the coupling section and this element and the light-emitting unit 5 passes along on the side of this element facing the axis of rotation 4. The element 23 consequently attenuates upon rotation of the rotor the primary radiation beam 8 only in the region of the coupling section.

FIG. 5a is an elevation of a first embodiment constructed as a neutral wedge filter, viewed from the axis 4. The transmission of the neutral wedge filter amounts on the lefthand and the righthand end to 100% and decreases towards the centre linearly to 50%. Both radiation beams 10a and 10b are thus damped simultaneously in the region of the coupling section.

Figure 5B:
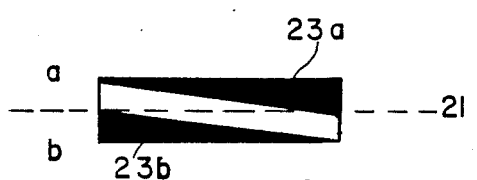

Another embodiment is shown in FIG. 5b. Here the cross-section of the primary radiation beam 8 is narrowed by two wedge-shaped diaphragms 23a and 23b to half the original cross-section. The upper diaphragm 23a is arranged so that the upper light beam is not absorbed at all on the lefthand edge of the element 23 and of the coupling section, respectively, whereas it is absorbed completely on the righthand edge of this element and of the coupling section, respectively. The wedge-shaped diaphragm 23b is arranged so that the light beam 10b is absorbed completely on the lefthand edge, whereas it is not absorbed at all on the righthand edge. This also applies to the embodiment shown in FIG. 5c.

Figure 5C:
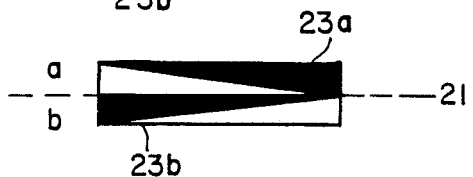

In FIG. 5b, however, the diaphragms are arranged so that they form a gap located obliquely with respect to the plane 21 and having a height which is half the vertical diameter of the radiation beam 8. As a result, a continuous change of tracks is forced to take place in the region of the coupling section, the data transmission between the light-emitting device and the light-receiving device passes from the radiation beam 10a to the radiation beam 10b, or conversely, in dependence upon the sense of rotation of the rotor. The embodiment shown in FIG. 5c is different in that the surface left free by the wedge-shaped diaphragm 23a above the plane 21 is symmetrical to the plane 21 with respect to the lower wedge-shaped diaphragm 23b, whereas the upper diaphragm 23a is symmetrical to the surface left free by the diaphragm 23b. This embodiment takes into account the particular form of the cross-section of the radiation beam 8 and is suitable for beam cross-sections having a symmetry which is a mirror image of the plane 21, for example, for circular and elliptical cross-sections.

The damping of a radiation beam is stronger according as this beam is reflected more frequently at the reflecting surface 2 in order to reach the coupling section. Thus, continuous periodical amplitude fluctuations are obtained at the output of the light-receiving device, which fluctuations are stronger according as the reflecting power of the reflecting surface 2 is smaller. These amplitude fluctuations can be suppressed simultaneously with the aforementioned amplitude jumps by a damping element which is fixedly arranged with respect to the hollow cylinder and which is arranged concentric to the axis 4 and encloses this axis completely in such a manner and whose damping is distributed along its circumference so that the intensi y of the beam 8 is damped so that an intensity is obtained at the input of the light-receiving device which is independent of the relative position of the hollow cylinder 1 and of the rotor 3.

It was assumed above that the hollow cylinder 1 is fixedly arranged and that the disc 3 is rotatable together with the light-emitting device 5 and the mirrors 9a and 9b. However, it is also possible for the disc 3 to be fixedly arranged and for the hollow cylinder 1 (together with the elements 12a . . . 17) to be rotated about the axis 4. It is only important that the two parts together with the components connected thereto are relatively rotatable.

The light-emitting device and the light-receiving device may also be mutually exchanged. In this case, the collector lenses 15a and 15b and the cylindrical lenses 13a and 13b can be omitted; instead, a cylindrical lens with a short focus has to be arranged in front of the light-receiving device. When the arrangement of FIG. 4 is used, an exchange is possible even without further steps being taken. The invention can be used especially in computer tomography apparatus for transmitting data from the rotating part to the fixedly arranged part, as is also known per se from the GE -OS 28 46 526. The region of the axis of rotation has then to be free from components (in this case an annular support can be used instead of the disc 3) and the hollow cylinder may have a considerable diameter (1 m). Nevertheless, pulses of a duration of a few ns can be transmitted thereby through a time distance of this order of magnitude.

What is claimed is:

1. Apparatus for transmitting signals between a first part and a second part which are relatively rotatable about an axis of rotation wherein:

the first part comprises a hollow cylinder with an axis which is disposed along the axis of rotation and having an inner reflective surface;

a portion of said second part is disposed within said hollow cylinder and reflective surface; and further comprising a light-emitting device;

a light-receiving device, a first of said light-emitting and light-receiving devices being affixed to the first part and the second of the light-emitting and light-receiving devices being affixed to the second part;

means for directing at least one beam of light from the light-emitting device onto the reflective inner surface of the cylinder at a grazing angle which is sufficiently small so that the beam(s) are repeatedly reflected by the inner surface along a path around and within the inner surface of the hollow cylinder without intervening reflection from portions of the second part which are contained within said hollow cylinder;

coupling section means, fixedly disposed with respect to the hollow cylinder and through which the light beam(s) are transmitted so that the first of the light-emitting and light-receiving devices is an optical connection with the second of the light-emitting or light-receiving devices from every possible relative position of the first part with respect to the second part.

2. Apparatus as claimed in claim 1 wherein the means for directing produces two beams of radiation from the light-emitting device which are reflected by the inner surface in opposite directions of rotation around the axis of rotation.

3. Apparatus as claimed in claim 1 or 2 further comprising a nonreflecting area on the inner surface of said cylinder which is disposed diametrically opposite from and is circumferentially smaller than the coupling section means.

4. Apparatus as claimed in claim 2 wherein the two beams of radiation are relatively displaced from each other in a direction parallel to the axis of rotation.

5. Apparatus as claimed in claim 4 wherein the coupling section means comprises two crossing curved mirrors which are relatively displaced from each other along the axis of rotation, each curved mirror having a length which approximately corresponds to the circumferential length of the coupling section means and each having a radius of curvature which is larger than the inner radius of the hollow cylinder, the curved mirrors being disposed so that the lines tangent to one end of each lie along tangents of the inner surface of the hollow cylinder.

6. Apparatus as claimed in claim 2 further comprising light attenuating means which are rigidly connected to the hollow cylinder adjacent to the coupling section means at a radial distance therefrom which is proportioned so that, upon relative rotation, the light attenuating means pass between the second of the light-emitting and light-receiving device and the two rotating beams and dampen the overall intensity of one or both of the beams passing through it.

7. The apparatus of claim 6 wherein light attenuating means comprise one or more neutral wedge filters.

8. The apparatus of claim 7 wherein the light attenuating means comprise one or more diaphragms.

9. Apparatus of claim 6 further comprising damping means disposed concentric to the axis of the cylinder around the full circumference thereof which dampen the light intensity around the full circumference of the circle so that the light-receiving device receives a constant radiation intensity from the light emitting device, independent of the relative positions of the rotatable parts.

* * * * *